(12) United States Patent
Worthington et al.

(10) Patent No.: US 9,554,641 B2
(45) Date of Patent: Jan. 31, 2017

(54) ORAL CARE IMPLEMENT

(71) Applicant: Colgate-Palmolive Company, New York, NY (US)

(72) Inventors: Brian G. Worthington, Dunellen, NJ (US); Sharon Kennedy, Randallstown, MD (US); Eduardo J. Jimenez, Manalapan, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 504 days.

(21) Appl. No.: 14/113,965

(22) PCT Filed: Oct. 7, 2013

(86) PCT No.: PCT/US2013/063678
§ 371 (c)(1),
(2) Date: Oct. 25, 2013

(87) PCT Pub. No.: WO2014/066021
PCT Pub. Date: May 1, 2014

(65) Prior Publication Data
US 2014/0119809 A1    May 1, 2014

Related U.S. Application Data

(60) Provisional application No. 61/719,016, filed on Oct. 26, 2012.

(51) Int. Cl.
*A46B 11/00* (2006.01)
*A46B 9/04* (2006.01)
(Continued)

(52) U.S. Cl.
CPC .......... *A46B 11/0093* (2013.01); *A46B 11/001* (2013.01); *A46B 11/0082* (2013.01); *A46B 15/0081* (2013.01)

(58) Field of Classification Search
CPC ... A46B 11/001; A46B 11/0082; A46B 11/00; A46B 2200/1066; B43K 5/00; A61C 17/02; A61C 117/30
(Continued)

(56) References Cited

U.S. PATENT DOCUMENTS

| 1,798,081 A | 3/1931 | Gordyn, Jr. et al. |
| 1,973,212 A | 9/1934 | Krueger |

(Continued)

FOREIGN PATENT DOCUMENTS

| AU | 2011 253 669 | 12/2011 |
| BE | 520830 | 7/1953 |

(Continued)

OTHER PUBLICATIONS

Anonymous, 2008, "Salviathymol N".
(Continued)

*Primary Examiner* — Mark A Laurenzi
*Assistant Examiner* — Thomas M Abebe (57) ABSTRACT

An oral care implement having an internal reservoir. In one embodiment, the invention can be a toothbrush comprising: a handle having an internal reservoir containing an oral care fluid; a head coupled to the handle; an applicator located on the head; a partition member positioned within the internal reservoir that divides the internal reservoir into a storage chamber and an overflow chamber; a passageway extending through the partition member from the storage chamber to the overflow chamber, the passageway terminating as a first opening in a first surface of the partition member and as a second opening in a second surface of the partition member; and a wick member having a first end in fluid communication with the applicator and a second end terminating in an
(Continued)

end surface that abuts the second surface of the partition member to prohibit axial movement of the wick member in a first axial direction.

26 Claims, 4 Drawing Sheets (51) Int. Cl.
A47L 13/22 (2006.01)
A46B 17/04 (2006.01)
A46B 15/00 (2006.01)

(58) Field of Classification Search
USPC .................... 401/199, 283, 99, 287, 284
See application file for complete search history.

(56) References Cited

U.S. PATENT DOCUMENTS

| | | | |
|---|---|---|---|
| 2,416,684 A | 3/1947 | Fischer | |
| 2,573,201 A | 10/1951 | Kelley et al. | |
| 2,594,721 A | 4/1952 | Beebe | |
| 2,739,328 A | 3/1956 | Bernier | |
| 2,964,012 A * | 12/1960 | Kahn | B43K 5/02 401/135 |
| 2,968,827 A * | 1/1961 | Lawsine | A46B 5/0033 132/311 |
| 3,369,543 A | 2/1968 | Ronco | |
| 3,459,483 A * | 8/1969 | Brastad | B43K 8/026 401/131 |
| 3,685,080 A | 8/1972 | Hubner | |
| 3,810,479 A | 5/1974 | Miles | |
| 3,902,510 A | 9/1975 | Roth | |
| 3,903,888 A | 9/1975 | Buelow et al. | |
| 3,910,706 A | 10/1975 | Del Bon | |
| 3,936,200 A | 2/1976 | O'Rourke | |
| 3,937,582 A | 2/1976 | Del Bon | |
| 4,023,580 A | 5/1977 | Pieters | |
| 4,060,870 A | 12/1977 | Cannarella | |
| 4,088,412 A | 5/1978 | Del Bon | |
| 4,124,316 A | 11/1978 | O'Rourke | |
| 4,181,997 A * | 1/1980 | O'Rourke | A61C 17/30 15/24 |
| 4,236,651 A | 12/1980 | Meyer et al. | |
| 4,304,245 A | 12/1981 | Lichfield | |
| 4,462,136 A | 7/1984 | Nakao et al. | |
| 4,486,109 A * | 12/1984 | Rosofsky | A46B 7/04 15/110 |
| 4,509,541 A | 4/1985 | Manciocchi, Jr. | |
| 4,521,128 A | 6/1985 | O'Neal | |
| 4,538,631 A | 9/1985 | Prince | |
| 4,543,679 A | 10/1985 | Rosofsky et al. | |
| 4,583,563 A * | 4/1986 | Turner | A46B 11/0024 132/311 |
| 4,585,018 A | 4/1986 | O'Connor | |
| 4,608,968 A * | 9/1986 | Rosofsky | A46B 7/04 401/132 |
| 4,716,035 A | 12/1987 | Sampathkumar | |
| 4,733,586 A | 3/1988 | Manusch et al. | |
| 4,753,249 A | 6/1988 | Muller | |
| 4,828,420 A | 5/1989 | Otsuka et al. | |
| 4,867,183 A | 9/1989 | Busch et al. | |
| 2,154,209 A | 8/1990 | Kohn | |
| 4,973,181 A | 11/1990 | Jankewitz | |
| 4,990,329 A | 2/1991 | Sampathkumar | |
| 5,000,193 A | 3/1991 | Heelis et al. | |
| 5,017,036 A | 5/1991 | Vidovic | |
| 5,033,898 A * | 7/1991 | Williams | A46B 11/0072 401/186 |
| 5,062,728 A * | 11/1991 | Kuo | A46B 11/0017 401/150 |
| 5,066,155 A | 11/1991 | English et al. | |
| 5,088,627 A | 2/1992 | Musel | |
| 5,094,254 A | 3/1992 | Krueckel et al. | |
| 5,096,319 A | 3/1992 | Gueret | |
| 5,098,297 A | 3/1992 | Chari et al. | |
| 5,102,251 A | 4/1992 | Kaufmann | |
| D337,659 S | 7/1993 | Lacy | |
| 5,309,590 A | 5/1994 | Giuliani et al. | |
| 5,346,324 A | 9/1994 | Kuo | |
| 5,352,052 A | 10/1994 | Kaufmann | |
| 5,393,153 A | 2/1995 | Bouthillier et al. | |
| 5,407,287 A | 4/1995 | Braun et al. | |
| 5,458,563 A | 10/1995 | Stewart | |
| 5,463,792 A | 11/1995 | Hogan et al. | |
| 5,476,384 A | 12/1995 | Giuliani et al. | |
| 5,490,529 A | 2/1996 | Fitjer | |
| 5,490,736 A | 2/1996 | Haber et al. | |
| 5,492,426 A | 2/1996 | Gueret | |
| 5,509,742 A | 4/1996 | Balzarini | |
| 5,578,023 A | 11/1996 | Schneider | |
| 5,611,687 A | 3/1997 | Wagner | |
| 5,769,553 A | 6/1998 | Chaudhri et al. | |
| 5,829,976 A | 11/1998 | Green | |
| 5,842,248 A | 12/1998 | van Grol et al. | |
| 5,865,195 A | 2/1999 | Carter | |
| 5,875,798 A | 3/1999 | Petrus | |
| 5,910,122 A | 6/1999 | D'Angelo | |
| 6,039,489 A | 3/2000 | Harman et al. | |
| 6,082,999 A | 7/2000 | Tcherny et al. | |
| 6,089,776 A | 7/2000 | Kaufmann | |
| 6,095,707 A | 8/2000 | Kaufmann | |
| 6,142,694 A | 11/2000 | Rivlin et al. | |
| 6,164,858 A | 12/2000 | Kaufmann | |
| 6,183,155 B1 | 2/2001 | Kaufmann | |
| 6,203,320 B1 | 3/2001 | Williams et al. | |
| 6,205,611 B1 | 3/2001 | Vigil | |
| 6,206,600 B1 | 3/2001 | Rosenberg et al. | |
| 6,244,774 B1 | 6/2001 | Barosso et al. | |
| 6,244,777 B1 | 6/2001 | Reid | |
| 6,322,268 B1 | 11/2001 | Kaufmann et al. | |
| 6,345,405 B1 | 2/2002 | Brackin | |
| 6,371,674 B1 | 4/2002 | Lerner | |
| 6,378,529 B1 | 4/2002 | Clemente Marco | |
| 6,416,242 B1 * | 7/2002 | Kaufmann | B05C 17/002 401/198 |
| 6,418,940 B1 | 7/2002 | Tcherny et al. | |
| 6,434,773 B1 | 8/2002 | Kuo | |
| D465,625 S | 11/2002 | Price | |
| 6,497,527 B2 | 12/2002 | Kaufmann | |
| 6,533,734 B1 | 3/2003 | Corley, III et al. | |
| RE38,150 E | 6/2003 | Greatbatch et al. | |
| 6,599,048 B2 | 7/2003 | Kuo | |
| 6,623,698 B2 | 9/2003 | Kuo | |
| 6,663,679 B1 | 12/2003 | Duncan | |
| 6,669,390 B1 | 12/2003 | Porter et al. | |
| 6,669,475 B2 | 12/2003 | Kandelman et al. | |
| 6,669,930 B1 | 12/2003 | Hoic et al. | |
| 6,770,266 B2 | 8/2004 | Santarpia, III et al. | |
| 6,802,097 B2 | 10/2004 | Hafliger et al. | |
| 6,817,803 B1 | 11/2004 | Ong et al. | |
| 6,895,629 B2 | 5/2005 | Wenzler | |
| 6,899,280 B2 | 5/2005 | Kotary et al. | |
| 6,902,337 B1 | 6/2005 | Kuo | |
| 6,932,603 B2 | 8/2005 | Han et al. | |
| 6,932,604 B2 | 8/2005 | Han et al. | |
| 510,482 A1 | 10/2005 | Jimenez | |
| 7,003,839 B2 | 2/2006 | Hafliger et al. | |
| 7,021,851 B1 | 4/2006 | King | |
| 7,025,521 B2 | 4/2006 | Tsaur | |
| 7,108,868 B2 | 9/2006 | Jia et al. | |
| 7,124,894 B1 | 10/2006 | Dobos | |
| 7,143,462 B2 | 12/2006 | Hohlbein | |
| 7,192,611 B2 | 3/2007 | Jia et al. | |
| 7,201,527 B2 | 4/2007 | Thorpe et al. | |
| 7,281,670 B2 | 10/2007 | Lakatos et al. | |
| 7,282,181 B2 | 10/2007 | Hudak et al. | |
| 7,303,143 B2 | 12/2007 | Davis et al. | |
| 7,311,456 B1 | 12/2007 | Neal | |
| 7,322,067 B2 | 1/2008 | Hohlbein | |
| 7,449,001 B2 | 11/2008 | Stoltz | |
| 7,478,960 B2 | 1/2009 | Glover | |
| 7,514,469 B2 | 4/2009 | Jia | |

(56) References Cited

U.S. PATENT DOCUMENTS

| | | | |
|---|---|---|---|
| 7,596,974 B2 | 10/2009 | Smith et al. | |
| 7,699,608 B2 | 4/2010 | Han et al. | |
| 7,722,278 B2 * | 5/2010 | Black | A46B 11/002 401/286 |
| 7,794,656 B2 | 9/2010 | Liang et al. | |
| 7,806,125 B2 | 10/2010 | Coopersmith | |
| 7,845,042 B2 | 12/2010 | Moskovich et al. | |
| 7,845,944 B2 | 12/2010 | DiGasbarro | |
| 8,398,326 B2 * | 3/2013 | Jimenez | A46B 11/0082 401/198 |
| 2001/0002228 A1 | 5/2001 | Owens | |
| 2002/0088473 A1 | 7/2002 | Fonseca et al. | |
| 2003/0045814 A1 | 3/2003 | Sangha | |
| 2003/0049327 A1 | 3/2003 | Zanone et al. | |
| 2003/0053938 A1 | 3/2003 | Szeles | |
| 2003/0086743 A1 | 5/2003 | Gruenbacher et al. | |
| 2003/0120180 A1 | 6/2003 | Kaylor et al. | |
| 2003/0157206 A1 | 8/2003 | Paek | |
| 2003/0194678 A1 | 10/2003 | Viltro et al. | |
| 2003/0224320 A1 | 12/2003 | Kandelman et al. | |
| 2004/0020508 A1 | 2/2004 | Earl | |
| 2004/0082878 A1 | 4/2004 | Baldwin et al. | |
| 2004/0097834 A1 | 5/2004 | Stoltz | |
| 2004/0182414 A1 | 9/2004 | Puskas | |
| 2004/0220498 A1 | 11/2004 | Li et al. | |
| 2004/0226575 A1 | 11/2004 | Hampton | |
| 2004/0237226 A1 | 12/2004 | Hohlbein et al. | |
| 2004/0255416 A1 | 12/2004 | Hohlbein et al. | |
| 2005/0019087 A1 | 1/2005 | Tsaur | |
| 2005/0026103 A1 | 2/2005 | Wasylucha | |
| 2005/0091769 A1 | 5/2005 | Jimenez et al. | |
| 2005/0115011 A1 | 6/2005 | Petit | |
| 2005/0147461 A1 | 7/2005 | Glover | |
| 2005/0201812 A1 | 9/2005 | Wong et al. | |
| 2005/0217688 A1 | 10/2005 | Liu et al. | |
| 2005/0218033 A1 | 10/2005 | Curtis | |
| 2005/0220530 A1 | 10/2005 | Carmona | |
| 2005/0221401 A1 | 10/2005 | Nomura et al. | |
| 2005/0232687 A1 | 10/2005 | Zeh et al. | |
| 2005/0233279 A1 | 10/2005 | Zeh et al. | |
| 2005/0244794 A1 | 11/2005 | Kemp et al. | |
| 2006/0026784 A1 | 2/2006 | Moskovich et al. | |
| 2006/0141421 A1 | 6/2006 | Braunecker et al. | |
| 2006/0225744 A1 | 10/2006 | Braunecker et al. | |
| 2006/0228163 A1 | 10/2006 | McSweeny | |
| 2006/0280548 A1 | 12/2006 | Sharpe | |
| 2007/0020032 A1 | 1/2007 | Abbas | |
| 2007/0086831 A1 | 4/2007 | Wold | |
| 2007/0151575 A1 | 7/2007 | DeMasi | |
| 2007/0154863 A1 | 7/2007 | Cai et al. | |
| 2007/0173738 A1 | 7/2007 | Stoltz | |
| 2007/0183838 A1 | 8/2007 | Umar | |
| 2007/0223988 A1 | 9/2007 | Gruenbacher et al. | |
| 2007/0255177 A1 | 11/2007 | Pronovost | |
| 2008/0014010 A1 | 1/2008 | Bartschi et al. | |
| 2008/0034524 A1 | 2/2008 | Takahashi | |
| 2008/0044791 A1 | 2/2008 | Tsurukawa et al. | |
| 2008/0176183 A1 * | 7/2008 | Gatzemeyer | A46B 11/001 433/82 |
| 2008/0201884 A1 | 8/2008 | Vazquez et al. | |
| 2009/0012425 A1 | 1/2009 | Dodge et al. | |
| 2009/0052972 A1 | 2/2009 | DellaCorte | |
| 2009/0060622 A1 | 3/2009 | Lian et al. | |
| 2009/0180826 A1 | 7/2009 | Guay | |
| 2009/0205674 A1 | 8/2009 | Saloff et al. | |
| 2009/0258326 A1 | 10/2009 | Al-Sulaiman et al. | |
| 2009/0261179 A1 | 10/2009 | Hall | |
| 2009/0317340 A1 | 12/2009 | Pak | |
| 2009/0320226 A1 | 12/2009 | Robinson et al. | |
| 2010/0331725 A1 | 12/2010 | Libby et al. | |
| 2011/0041275 A1 * | 2/2011 | Gatzemeyer | A46B 11/0093 15/210.1 |
| 2011/0214240 A1 * | 9/2011 | Jimenez | A46B 11/0082 15/167.1 |
| 2012/0275841 A1 * | 11/2012 | Jimenez | A46B 11/0006 401/140 |

FOREIGN PATENT DOCUMENTS

| | | |
|---|---|---|
| CN | 2343878 | 10/1999 |
| DE | 3113450 | 10/1982 |
| DE | 3832520 | 4/1990 |
| DE | 4139141 | 6/1993 |
| DE | 10035214 | 2/2002 |
| DE | 202004008909 | 9/2004 |
| EP | 0092359 | 10/1983 |
| EP | 0097904 | 1/1984 |
| EP | 0244363 | 11/1987 |
| EP | 0373758 | 6/1990 |
| EP | 0631771 | 1/1995 |
| EP | 1053744 | 11/2000 |
| EP | 1095660 | 5/2001 |
| EP | 1270580 | 1/2003 |
| EP | 1639913 | 3/2006 |
| EP | 2174649 | 4/2010 |
| FR | 2452277 | 10/1980 |
| FR | 2777459 | 10/1999 |
| GB | 842965 | 8/1960 |
| GB | 2205280 | 12/1988 |
| GB | 2394653 | 5/2004 |
| GB | 2430146 | 3/2007 |
| JP | 1-097406 | 4/1989 |
| JP | 2-43099 | 2/1990 |
| JP | 2-152405 | 6/1990 |
| JP | 2-297498 | 12/1990 |
| JP | 9-215524 | 8/1997 |
| JP | 2003-019023 | 1/2003 |
| JP | 2003-250631 | 9/2003 |
| JP | 2004-108858 | 4/2004 |
| JP | 2005-257604 | 9/2005 |
| KR | 20-0183429 | 5/2000 |
| NL | 9400631 | 12/1995 |
| RU | 2105519 | 2/1998 |
| RU | 2239342 | 11/2004 |
| TW | 200605814 | 2/2006 |
| WO | WO 92/10146 | 6/1992 |
| WO | WO 95/17159 | 6/1995 |
| WO | WO 99/05987 | 2/1999 |
| WO | WO 01/62082 | 8/2001 |
| WO | WO 03/000506 | 1/2003 |
| WO | WO 2005/009352 | 2/2005 |
| WO | WO 2006/019289 | 2/2006 |
| WO | WO 2006/032367 | 3/2006 |
| WO | WO 2007/011552 | 1/2007 |
| WO | WO 2007/073917 | 7/2007 |
| WO | WO 2008/091935 | 7/2008 |
| WO | WO 2011/106017 | 9/2011 |
| WO | WO 2012/105961 | 8/2012 |
| WO | WO 2012/134435 | 10/2012 |

OTHER PUBLICATIONS

Anonymous, 2012, "Betaisodona-Mund-Antiseptikum".

Ciobanu et al., "Antimicrobial Mouthwash Concentrate—Inhibiting Cariogenic Buccal Flora Comprises Alcoholic Extract of Plants, Volatile Oils and Propolis Tincture," WPI Thomson AN 1993-203503.

Hyssopbrush, 2013, product description on CDM Supply website, http://cdmsupply.com/product_info.php?cPath=44&products_id=130.

International Search Report and Written Opinion in International Application No. PCT/US10/043825, mailed Apr. 28, 2011.

International Search Report and Written Opinion in International Application No. PCT/US11/027740, mailed Jan. 17, 2012.

International Search Report and Written opinion in International Application No. PCT/US2009/054582, mailed Aug. 3, 2010.

(56) References Cited

OTHER PUBLICATIONS

International Search Report and Written Opinion of corresponding International Application No. PCT/US2010/025605 dated Nov. 19, 2010.
International Search Report and Written Opinion of International Application No. PCT/US2008/051778 dated Dec. 12, 2008.
International Search Report and Written Opinion of International Application No. PCT/US2011/027042 mailed Nov. 28, 2011.
Office Action from the Taiwan Intellectual Property Office, dated Apr. 7, 2011, for corresponding Taiwan Patent Application No. 97102421.
Squirtbrush, 2013, product description on CDM Supply website, http://cdmsupply.com/product_info.php?cPath=42&products_id=109.
Written Opinion for PCT/US2010/025605 mailed on Mar. 1, 2012.
Written Opinion in International Application No. PCT/US11/027042, mailed Jul. 10, 2012.

\* cited by examiner

ORAL CARE IMPLEMENT

CROSS-REFERENCE TO RELATED PATENT APPLICATIONS

The present application is a U.S. national stage application under 35 U.S.C. §371 of PCT Application No. PCT/US2013/063678, filed Oct. 7, 2013, which claims the benefit of U.S. Provisional Patent Application No. 61/719,016, filed Oct. 26, 2012, the entireties of which are hereby incorporated by reference.

FIELD OF THE INVENTION

The present invention relates generally to oral care implements, and specifically to oral care implements having a reservoir that stores an oral care agent.

BACKGROUND OF THE INVENTION

Oral care implements, particularly toothbrushes, are typically used by applying toothpaste to a bristle section followed by brushing regions of the oral cavity such as the teeth, tongue and/or gums. Some oral care implements are equipped with built-in fluid reservoirs and systems for delivering dentifrice and other oral care agents to the bristle section of the oral care implement. There is a continuing need, however, for improved oral care implements for dispensing dentifrice and other oral care agents from the implement.

BRIEF SUMMARY OF THE INVENTION

The present invention is directed to an oral care implement having an internal reservoir and an end cap. In one aspect, the oral care implement includes a handle comprising the internal reservoir that contains an oral care fluid and a head coupled to the handle. An end cap is coupled to the handle in a manner that prevents leakage of the oral care fluid from the reservoir.

In one embodiment, the invention can be a toothbrush comprising: a handle extending along a longitudinal axis and having an internal reservoir containing an oral care fluid; a head coupled to the handle and having a plurality of tooth cleaning elements; an applicator located on the head; a partition member positioned within the internal reservoir that divides the internal reservoir into a storage chamber and an overflow chamber, the partition member comprising a first surface facing the storage chamber and a second surface facing the overflow chamber; a passageway extending through the partition member from the storage chamber to the overflow chamber, the passageway terminating as a first opening in the first surface of the partition member and as a second opening in the second surface of the partition member; and a wick member having a first end in fluid communication with the applicator and a second end terminating in an end surface that abuts the second surface of the partition member to prohibit axial movement of the wick member in a first axial direction.

In another embodiment, the invention can be a toothbrush comprising: a handle extending along a longitudinal axis and having an internal reservoir containing an oral care fluid; a head coupled to the handle and having a plurality of tooth cleaning elements; an applicator located on the head; a partition member positioned within the internal reservoir, the partition member separating the internal reservoir into a storage chamber and an overflow chamber, a passageway formed through the partition member and comprising an inlet section and a delivery section, the inlet section extending from the storage chamber to the delivery section, the delivery section extending from the inlet section to the overflow chamber, and wherein the inlet section has a transverse cross-sectional area that is greater than a transverse cross-sectional area of the delivery section; and a wick member having a first end in fluid communication with the applicator and a second end in fluid communication with the delivery section.

In yet another embodiment, the invention can be a toothbrush comprising: a handle extending along a longitudinal axis and having an internal reservoir containing an oral care fluid; a head coupled to the handle and having a plurality of tooth cleaning elements; an applicator located on the head; a partition member positioned within the internal reservoir that divides the internal reservoir into a first chamber and a second chamber, the partition member comprising a first surface facing the first chamber and a second surface facing the second chamber; a passageway extending through the partition member from the first chamber to the second chamber, the passageway terminating as a first opening in the first surface of the partition member and as a second opening in the second surface of the partition member; and a wick member having a first end in fluid communication with the applicator and a second end terminating in an end surface having an outer perimeter that surrounds the second opening.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Figure 1:
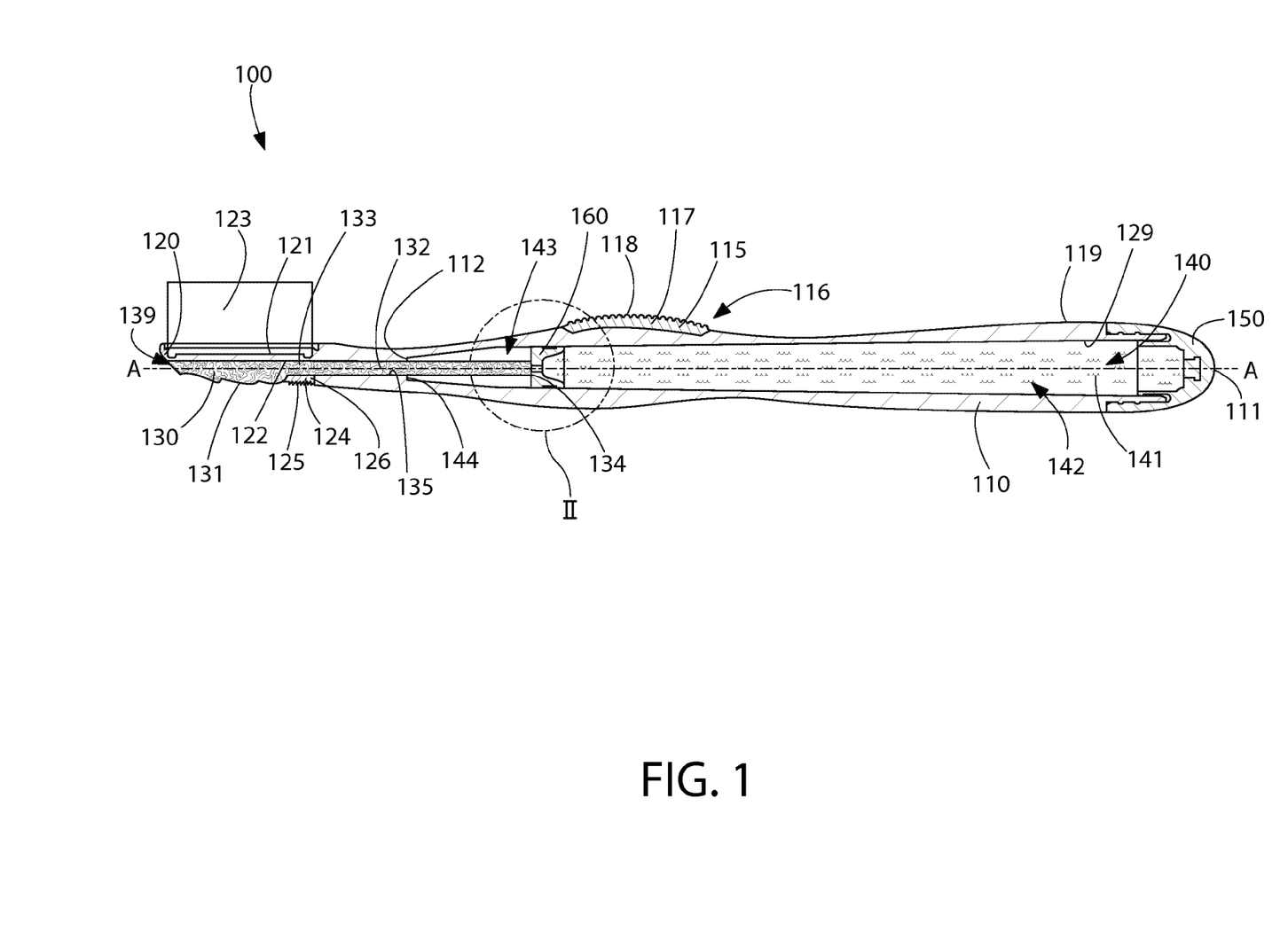
FIG. 1 is a cross-sectional view of an oral care implement in accordance with an embodiment of the present invention.

Referring first to FIG. 1, an oral care implement 100 will be described in accordance with an embodiment of the present invention. In the exemplified embodiment, the oral care implement 100 is in the form of a manual toothbrush. However, in certain other embodiments the oral care implement 100 can take on other forms such as being a powered toothbrush, a tongue scraper, a gum and soft tissue cleanser, a water pick, an interdental device, a tooth polisher, a specially designed ansate implement having tooth engaging elements or any other type of implement that is commonly used for oral care. Thus, it is to be understood that the inventive concepts discussed herein can be applied to any type of oral care implement unless a specific type of oral care implement is specified in the claims.

The oral care implement generally comprises a handle 110 extending along a longitudinal axis A-A from a proximal end 111 to a distal end 112 and a head 120 coupled to the distal end 112 of the handle 110. Furthermore, an end cap 150 is coupled to the proximal end 111 of the handle 110. The handle 110 is an elongated structure that provides the mechanism by which the user can hold and manipulate the oral care implement 100 during use. The handle 110 has a generic shape with various contours, none of which are specifically limiting of the present invention. Furthermore, the handle 110 also comprises an inner surface 129 that defines an internal reservoir 140 containing an oral care fluid 141 therein and an outer surface 119 that is gripped by a user during use of the oral care implement 100. The end cap 150 is coupled to the handle to prevent the oral care fluid 141 from leaking out of the internal reservoir 140.

In certain embodiments, the end cap 150 is removably coupled to the handle 110 so that the oral care fluid 141 contained within the internal reservoir 140 can be refilled upon depletion thereof. In such embodiments, with the end cap 150 removed from the handle 110 a user can refill the internal reservoir 140 with any desired oral care fluid 141, including the different types of oral care fluids discussed below. However, in certain other embodiments the end cap 150 may be permanently affixed to the handle 110. In such embodiments, upon depletion of the oral care fluid 141 the oral care implement 100 can either be used as a standard oral care implement 100 without the benefits of the oral care fluid 141, or the oral care implement 100 can be discarded.

In the exemplified embodiment, the internal reservoir 140 extends along the axial length of the handle 110 of the oral care implement 100. Thus, the internal reservoir 140 is capable of containing an amount of the oral care fluid 141 that is sufficient for multiple uses. Of course, in other embodiments the internal reservoir 140 may be smaller and only extend partially along the axial length of the handle 110. In certain such embodiments, the reservoir 140 may only include enough of the oral care fluid 141 for a single use of the oral care implement 100. In such embodiments, the oral care implement 100 can either be a disposable oral care implement that is discarded after one use, or the internal reservoir 140 can be refilled between uses as desired.

A partition member 160 is positioned within the internal reservoir 140. The partition member 160 divides the internal reservoir 140 into a storage chamber 142 and an overflow chamber 143. The storage chamber 142 is the portion of the internal reservoir 140 that stores the oral care fluid 141 prior to use thereof and the overflow chamber 143 contains excess of the oral care fluid 141. Under normal conditions, all of the oral care fluid 141 is stored within the storage chamber 142 and the overflow chamber 143 is free of the oral care fluid 141. When an expansion takes place within the storage chamber 142, such as due to altitude or temperature fluctuations, a portion of the oral care fluid 141 in the storage chamber 142 will flow into the overflow chamber 143. Specifically, temperature fluctuations and altitude fluctuations cause air volume fluctuations within the storage chamber 142, which will cause the oral care fluid 141 to flow from the storage chamber 142 into the overflow chamber 143. Furthermore, the overflow chamber 143 captures any of the oral care fluid 141 that drips off of the wick member 132 (discussed below). The details of the partition member 160 and the internal reservoir 140 will be discussed in more detail below with reference to FIG. 2. In certain embodiments, the excess oral care fluid 141 in the overflow chamber 143 will return to the storage chamber 142 when the pressure or expansion in the storage chamber 142 subsides.

Furthermore, while the invention is discussed below (and above) in terms of the partition member 160 dividing the internal reservoir 140 into a storage chamber 142 and an overflow chamber 143, in certain embodiments of the invention in which overflow is not of concern, the partition member 160 may simply divide the internal reservoir 140 into a first chamber and a second chamber. In such an embodiment, the partition member 140 will serve its function of ensuring correct axial positioning of the wick member.

The oral care fluid 141 contained within the reservoir 140 is a material that provides oral health benefits to a user upon contact with a user's oral cavity. In one embodiment, the oral care fluid 141 is a fluidic material. For example, in certain embodiments the oral care fluid 141 is a mouthwash solution that cleans the oral surfaces when applied thereto and provides the user with breath freshening benefits. In other embodiments, the oral care fluid 141 is a tooth cleaning solution, such as a dentifrice. Of course, the oral care fluid 141 is not to be in any way limiting of the present invention and may include fluids having active or inactive agents that deliver therapeutic, cosmetic, experiential and/or sensorial benefits to a consumer during a tooth, soft tissue, tongue or interdental cleaning regimen. Specifically, the oral care material can be an anti-sensitivity agent, fluoride, a tartar protection agent, an antibacterial agent, an oxidative or whitening agent, an enamel strengthening or repair agent, a tooth erosion preventing agent, a tooth sensitivity ingredient, a gum health active, a nutritional ingredient, a tartar control or anti-stain ingredient, an enzyme, a sensate ingredient, a flavor or flavor ingredient, a breath freshening ingredient, an oral malodor reducing agent, an anti-attachment agent or sealant, a diagnostic solution, an occluding agent, a dry mouth relief ingredient, a catalyst to enhance the activity of any of these agents, colorants or aesthetic ingredients, arginine bicarbonate, chlorohexidine, triclosan, CPC, zinc oxide and combinations thereof. In certain embodiments, the oral care fluid 141 is free of a dentifrice as the oral care fluid 141 is intended to supplement traditional brushing of the teeth rather than supplant it (hence its delivery to the rear surface of the head as opposed to the bristles in certain embodiments, as discussed below).

The head 120 of the oral care implement 100 comprises a front surface 121 and an opposing rear surface 122. A plurality of tooth cleaning elements 123 extend from the front surface 121 of the head 120. In the exemplified embodiment, the tooth cleaning elements 123 are generically illustrated as a block. The exact structure, pattern, orientation and material of the tooth cleaning elements 123 is not to be limiting of the present invention unless so specified in the claims. Thus, as used herein, the term "tooth cleaning elements" is used in a generic sense to refer to any structure that can be used to clean, polish or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth cleaning elements 123 of the present invention can be connected to the head 120 in any manner known in the art. For example, staples/anchors, in-mold tufting (IMT) or anchor free tufting (AFT) could be used to mount the cleaning elements/tooth engaging elements. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

In the exemplified embodiment, a soft tissue cleanser 124 is positioned on and coupled to the rear surface 122 of the head 120. The soft tissue cleanser 124 comprises a pad portion 126 and a plurality of protuberances 125 protruding from the pad portion 126. In the exemplified embodiment, each of the plurality of protuberances 125 is in the form of a nub. As used herein a "nub" generally refers to a column-like protrusion (without limitation to the cross-sectional shape of the protrusion) which is upstanding from a base surface. In a general sense, the protuberances 125 in the preferred construction have a height that is greater than the width at the base of the protuberance 125 (as measured in the longest direction). Nevertheless, protuberances or nubs could include projections wherein the widths and heights are roughly the same or wherein the heights are somewhat smaller than the base widths. Moreover, in some circumstances (e.g., where the protuberances taper to a tip or include a base portion that narrows to a smaller projection), the base width can be substantially larger than the height.

In one preferred arrangement of the soft tissue cleanser 124, the plurality of protuberances 125 are preferably conically shaped. As used herein, "conically shaped" or "conical" is meant to include true cones, frusto-conically shaped elements, and other shapes that taper to a narrow end and thereby resemble a cone irrespective of whether they are uniform, continuous in their taper, or have rounded cross-sections. In the exemplified embodiment, the soft tissue cleanser 124 including the pad 126 and the protuberances 125 are formed from a resilient material, such as an injection molded thermoplastic elastomer. Without intending to be limited, an example of a suitable elastomeric soft tissue cleanser that may be used with the present invention and positioned on the rear surface 122 of the head 120 is disclosed in U.S. Pat. No. 7,143,462, issued Dec. 5, 2006 to the assignee of the present application, the entirety of which is hereby incorporated by reference. In certain other embodiments, the protuberances 125 of the soft tissue cleanser 124 can take the form of elongated ridges, nubs, or combinations thereof. Furthermore, the invention is not limited to an embodiment that incorporates a soft tissue cleanser 124 on the rear surface 122 of the head 120 and in certain other embodiments the soft tissue cleanser 124 may be omitted.

In the exemplified embodiment, the handle 110 and the head 120 are integrally formed as a single unitary structure using a molding, milling, machining or other suitable process. However, the invention is not to be so limited and in certain other embodiments the handle 110 and the head 120 can be separately formed components that are operably coupled at a later stage of the manufacturing process by any suitable technique known in the art, including without limitation thermal or ultrasonic welding, a tight-fit assembly, a coupling sleeve, threaded engagement, adhesion, or fasteners.

In certain embodiments, each of the handle 110 and the head 120 are formed of a rigid material, such as for example without limitation polymers and copolymers of ethylene, propylene, butadiene, vinyl compounds and polyesters such as polyethylene terephthalate. Of course, the invention is not to be so limited in all embodiments and in certain other embodiments the handle 110 and/or the head 120 can be formed of other materials. Furthermore, in the exemplified embodiment the end cap 150 is also formed of a rigid material, such as one of the example materials listed above. However, the invention is not to be so limited and the end cap 150 can be formed of other materials, including resilient materials and non-plastic rigid materials such as wood, metal or the like.

In the exemplified embodiment, the handle 110 includes a grip component 115 in a thumb-grip region 116 of the handle 110. The grip component 115 is formed of a resilient material, such as a thermoplastic elastomer, and is coupled to the handle 110 via a technique known in the art such as injection molding or the like. The grip component 115 enhances user comfort when gripping the oral care implement 100 and minimizes or reduces the likelihood of a user's hand slipping on the handle 110 during use of the oral care implement 100 in a wet toothbrushing environment. In the exemplified embodiment, the grip component 115 is only located on a front surface of the handle 110. However, the invention is not to be so limited in all embodiments and in certain other embodiments the grip component 115 may also be positioned on a rear surface and/or along the side surfaces of the handle 110.

The grip component 115 includes a body portion 117 and a plurality of protuberances 118 extending outwardly from the body portion 117. In certain embodiments, the protuberances 118 are nubs extending from the body portion 117 of the grip component 115, such as the nubs discussed above with regard to the soft tissue cleanser 124. Of course, the invention is not to be so limited in all embodiments and the protuberances 118 can take on other shapes and forms such as being columnar protrusions, elongate ridges extending along the width of the body portion 117 of the grip component 115 or the like. The protuberances 118 provide an additional surface for preventing slippage during use of the oral care implement and for enhanced comfort.

In addition to the grip component 115, the handle 110 may be formed with additional resilient materials covering portions of or the entirety of the handle 110 to further enhance the gripability of the handle 110 during use. For example, portions of the handle 110 that are typically gripped by a user's palm during use may be overmolded with a thermoplastic elastomer or other resilient material to further increase comfort to a user. The exact shape, contour and resilient material coverings on the handle 110 are not to be limiting of the present invention unless specifically claimed.

The head 120 of the oral care implement 100 further comprises an applicator 130 located on the rear surface 122 of the head 120. Specifically, the applicator 130 is located on the surface of the head 120 opposite the tooth cleaning elements 123. Of course, the invention is not to be so limited and in certain other embodiments the location of the applicator 130 is not limited to the rear surface 122 of the head 120. Specifically, in certain other embodiments the applicator 130 may be located within the field of the plurality of tooth cleaning elements 111 on the front surface 121 of the head 120 or on any other desired region of the head 120 of the oral care implement 100. Furthermore, in still other embodiments the applicator 130 may be located on the handle 110 or elsewhere on the oral care implement 100.

In the exemplified embodiment, the applicator 130 is surrounded by or embedded within the soft tissue cleanser 124. Furthermore, in the exemplified embodiment the applicator 130 has projections 131 that are exposed and contact a user's teeth and/or gums during use of the oral care implement 100. The projections 131 are formed integrally with the applicator 130 and follow the contours of the projections 125 of the soft tissue cleanser 124 to further enhance the cleaning of the user's teeth and/or gums.

The head 120 of the oral care implement 100 further comprises a wick member 132 having a first end 133 that is in fluid communication with the applicator 130 and a second end 134 that is in fluid communication with the oral care fluid 141 contained within the internal reservoir 140. At least a portion of the wick member 132 is located within a channel 135 that is formed through the head 120 of the oral care implement 100 from a distal end 144 of the overflow chamber 143 of the internal reservoir 140 to the applicator 130. More specifically, in the exemplified embodiment the applicator 130 is exposed through an opening 139 on the rear surface 122 of the head 120. Thus, the channel 135 extends from the distal end 144 of the overflow chamber 143 to the opening 139 on the rear surface 122 of the head 120. The channel 135 provides a passageway through the oral care implement 100 from the internal reservoir 140 to the rear surface 122 of the head 120 where the applicator 130 is exposed for contact with a user's teeth and gums during use of the oral care implement 100. The exact positioning and location of the second end 134 of the wick member 132 will be discussed in more detail below with reference to FIGS. 2-4.

In the exemplified embodiment, the wick member 132 has a cylindrical cross-sectional profile. However, the invention is not to be so limited in all embodiments and in certain other embodiments the wick member 132 may have other cross-sectional profiles. In the exemplified embodiment, the wick member 132 is integrally formed with the applicator 130 out of a capillary material, including without limitation, a fibrous material, ceramic, porous plastic or combinations thereof. Thus, in the exemplified embodiment the oral care fluid 141 in the internal reservoir 140 is delivered to the applicator 130 solely by capillary action through the wick member 132. In certain other embodiments, the applicator 130 and the wick member 132 can be separately formed out of two different types of the capillary materials discussed above. In such embodiments, the oral care fluid 141 may flow through each of the wick member 132 and the applicator 130 at different flow rates depending on the material and pore size distribution of each component.

For example, the oral care fluid 141 may flow at a faster rate from the internal reservoir 140 onto the wick member 132 than from the wick member 132 onto the applicator 130 to prevent overdosing the oral care fluid 141 onto the user's teeth and/or gums during use of the oral care implement 100. In this manner, the dose of the oral care fluid 141 applied to a user's teeth and/or gums is the amount of oral care fluid 141 saturating the applicator 130. In other words, during use of the oral care implement 100 the oral care fluid 141 on the applicator 130 will become depleted. It will take some amount of time, such as ten minutes, thirty minutes, one hour, two hours or more for the applicator 130 to become re-saturated with the oral care fluid 141. Thus, once the dosage of oral care fluid 141 on the applicator 130 is depleted, the user will not be able to apply more of the oral care fluid 141 onto her teeth and/or gums until the time period has expired and the applicator 130 is again saturated with the oral care fluid 141.

In certain embodiments the wick member 132 may comprise a first portion having a first capillarity and a second portion having a second capillarity such that the first and second capillarities are different. In certain embodiments the first and second sections of the wick member 132 may be axial segments of the wick member 132. In other embodiments, the second portion of the wick member 132 may be a sleeve that circumferentially surrounds the first portion of the wick member 132. The different capillarities of the first and second portions of the wick member 132 causes each of the first and second portions of the wick member 132 to transmit fluid through those portions at different rates (i.e., the first and second portions of the wick member 132 have different wicking rates). The different capillarities of the first and second portions of the wick member 132 can be achieved by utilizing a different pore size distribution, a different pore density, a combination of different pore sizes and pore densities, or using different materials for the first and second portions of the wick member 132.

As noted above, the materials that form the applicator 130 and the wick member 132 includes fibrous materials, ceramics and porous plastics, such as those available from Porex Technologies, Atlanta, Ga. One example of a fibrous material is an acrylic material identified as type number C10010, available from Teibow Hanbai Co., Ltd., Tokyo, Japan. A mixture of porous and/or fibrous materials may be provided which have a distribution of larger and smaller capillaries. The applicator 130 and the wick member 132 can be formed from a number of small capillaries that are connected to one another, or as a larger single capillary tube. Furthermore, although delivery of the oral care fluid 141 from the internal reservoir 140 to the applicator 130 is described herein as being accomplished solely by capillary action, in certain other embodiments delivery may be achieved via mechanical action, mechanical pumps and/or electrical pumps or combinations thereof either solely or in addition to the capillary action.

Figure 2:
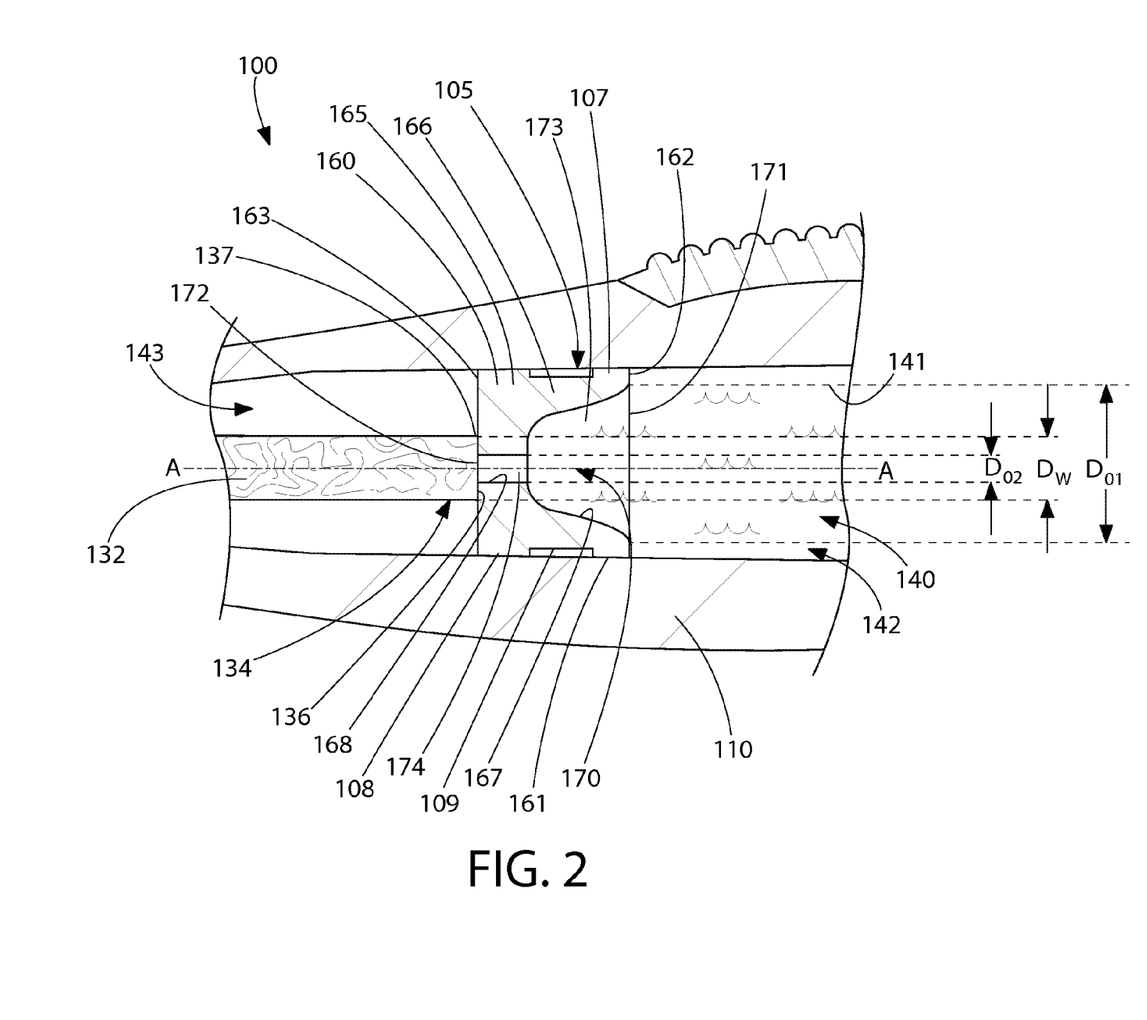
FIG. 2 is a close-up of area II of FIG. 1.

Referring now to FIG. 2, a close-up view of area II of FIG. 1 is illustrated. FIG. 2 illustrates a close-up view of the partition member 160 within the internal reservoir 140. As noted above, the partition member 160 is a structural member that is positioned within the internal reservoir 140 to separate the internal reservoir 140 into the storage chamber 142 and the overflow chamber 143. The partition member 160 is positioned at a fixed axial location within the internal reservoir 140, which assists with ensuring that all components of the oral care implement 100 are located at the same position each time that the oral care implement is assembled 100. Specifically, by locating the partition member 160 at a fixed axial location within the internal reservoir 140 and by fixing the lengths of the wick member 132 and applicator 130, it can be ensured that all components are at the same position each time the oral care implement 100 is assembled.

In certain embodiments, the partition member 160 is positioned within the internal reservoir 140 by an interference fit such that the partition member 160 is pressed into the internal reservoir 140 until an outer surface 161 of the partition member 160 fits snugly against the inner surface 129 of the handle 110 that defines the internal reservoir 140. In this manner, the partition member 160 is static and non-movable within the internal reservoir 140. In the exemplified embodiment, the outer surface 161 of the partition member 160 comprises a first annular projection 107 and a second annular projection 108. The first and second annular projections 107, 108 are spaced from one another thereby forming a recessed region 109 on the outer surface 161 of the partition member 160. Thus, the outer surface 161 of the partition member 160 is a stepped surface. While the first and second annular projections 107, 108 of the outer surface 161 of the partition member 160 are in abutment with the inner surface 129 of the handle 110, the recessed region 109 of the outer surface 161 of the partition member 160 is spaced from the inner surface 129 of the handle 110 by a gap 105. Of course, the invention is not to be so limited by this structural arrangement in all embodiments and in certain other embodiments the outer surface 161 of the partition member 160 may be a non-stepped surface.

Furthermore, the invention is not to be limited by an interference fit between the partition member 160 and the inner surface 129 of the handle 110 in all embodiments, and in certain other embodiments the partition member 160 may be stationarily positioned within the internal reservoir 140 by other techniques, such as adhesion, fasteners, threaded engagement, tight-fit assembly, ultrasonic or thermal welding, or a coupling sleeve. The partition member 160 can be formed from a variety of different types of materials, including without limitation polypropylene, low and high density polyethylene, thermoplastic elastomer and thermoplastic vulcanizate. Of course, the invention is not to be so limited and materials other than those mentioned herein can be used to form the partition member 160 in other embodiments.

The partition member 160 comprises a first surface 162 facing the storage member 142 and a second surface 163 facing the overflow chamber 163. In the exemplified embodiment, each of the first and second surfaces 162, 163 of the partition member 160 are transverse surfaces. Specifically, each of the first and second surfaces 162, 163 of the partition member 160 are transverse to and oriented at a normal angle relative to the longitudinal axis A-A of the handle 110.

Furthermore, a passageway 170 extends through the partition member 160 from the storage chamber 142 to the overflow chamber 143. The passageway 170 terminates as a first opening 171 in the first surface 162 of the partition member 160 and as a second opening 172 in the second surface 163 of the partition member 160. Thus, the oral care fluid 141 in the internal reservoir 140 flows from the storage chamber 142 through the first opening 171 in the first surface 162 of the partition member 160, through the passageway 170 and then through the second opening 172 in the second surface 163 of the partition member 160 where it contacts the wick member 132. In the exemplified embodiment, the first opening 171 has a diameter $D_{O1}$ and the second opening 172 has a diameter $D_{O2}$ such that the diameter $D_{O1}$ of the first opening 171 is greater than the diameter $D_{O2}$ of the second opening 172.

The passageway 170 comprises an inlet section 173 and a delivery section 174. The inlet section 173 of the passageway 170 and the delivery section 174 of the passageway 170 are in fluid communication with one another, and the delivery section 174 and the inlet section 173 collectively form the entire passageway 170. The inlet section 174 comprises the first opening 171 and extends from the storage chamber 142 to the delivery section 174 and terminates at the first opening 171. The delivery section 174 comprises the second opening 172 and extends from the inlet section 173 to the overflow chamber 143 and terminates at the second opening 172. In the exemplified embodiment, the inlet section 173 has a maximum transverse cross-sectional area that is greater than a maximum transverse cross-sectional area of the delivery section 174. Thus, the delivery section 174 is narrower than the inlet section 173 and prevents excess amounts of the oral care fluid 141 from flowing through the delivery section 174 and into contact with the wick member 132. By being a narrowed section of the passageway 170, the delivery section 174 minimizes the amount of the oral care fluid 141 that is able to exit the storage chamber 142 and reduces the likelihood of overdosing the wick member 132 with the oral care fluid 141.

Conceptually, the partition member 160 comprises an upper section 165 and an annular sidewall 166 extending from the upper section 165 in a direction towards the storage chamber 142. The annular sidewall 166 of the partition member 160 comprises an inner surface 167 that defines the inlet section 173 of the passageway 170. In the exemplified embodiment, the inner surface 167 of the annular sidewall 166 of the partition member 160 is a concave surface facing the storage chamber 142. Thus the cross-sectional area of the inlet section 173 of the passageway 170 decreases with distance from the storage chamber 142. However, the invention is not to be so limited in all embodiments and in certain other embodiments the cross-sectional area of the inlet section 173 of the passageway can be constant.

Furthermore, the upper section 165 of the partition member 160 comprises an inner surface 168 that defines the delivery section 174 of the passageway 170. In the exemplified embodiment, the cross-sectional area of the delivery section 174 of the passageway 170 is constant. However, the invention is not to be so limited in all embodiments and in certain other embodiments the cross-sectional area of the delivery section 174 of the passageway 170 may increase and/or decrease with distance from the inlet section 173 of the passageway 170. Specifically, in certain embodiments the cross-sectional area of the delivery section 174 of the passageway 170 may decrease with distance from the inlet section 173 of the passageway 170 in order to further limit the amount of the oral care fluid 141 that is able to contact the wick member 132.

The wick member 132 extends from the applicator 130, through the channel 135 and into the overflow chamber 143. More specifically, the second end 134 of the wick member 132 terminates in an end surface 136 that abuts the second surface 163 of the partition member 160. Due to the abutment of the end surface 136 of the second end 134 of the wick member 132 against the second surface 163 of the partition member 160, axial movement of the wick member 132 in a first axial direction towards the storage chamber 142 is prohibited.

In the exemplified embodiment, the end surface 136 of the second end 134 of the wick member 132 abuts against the second surface 163 of the partition member 160 at a location such that the end surface 136 of the second end 134 of the wick member 132 covers the second opening 172 in the second surface 163 of the partition member 160. As a result, as the oral care fluid 141 flows through the passageway 170 and through the second opening 172, the oral care fluid 141 comes directly into contact with the wick member 132. Due to the material that forms the wick member 132 as discussed above, the oral care fluid 141 is then soaked up by the wick member 132 and flows along the wick member 132 towards the applicator 130 via capillary action where the oral care fluid 141 is dispensed onto a user's tongue, gums, teeth and other oral surfaces during use of the oral care implement 100. In the exemplified embodiment, the end surface 136 of the second end 134 of the wick member 132 is a transverse surface. However, the invention is not to be so limited in all embodiments as will be discussed in more detail below with reference to FIG. 4.

Although the exemplified embodiment illustrates the end surface 136 of the second end 134 of the wick member 132 covering the second opening 172, in alternate embodiments the end surface 136 of the second end 134 of the wick member 132 may not cover the second opening 172. Specifically, in other embodiments the end surface 136 of the second end 134 of the wick member 132 may abut the second surface 163 of the partition member 160 while being positioned adjacent to the second opening 172. In such embodiments, the oral care fluid 141 will flow through the second opening 172 and into the overflow chamber 143 where it will contact the wick member 132.

The end surface 136 of the second end 134 of the wick member 132 has an outer perimeter 137 having a diameter $D_W$. In the exemplified embodiment, the diameter $D_W$ of the end surface 136 of the second end 134 of the wick member 132 is greater than the diameter $D_{O2}$ of the second opening 172. Thus, in this embodiment the end surface 136 of the second end 134 of the wick member 132 is prevented from penetrating through the second opening 172 and into the delivery section 174 of the passageway 170 because the end surface 136 of the second end 134 of the wick member 132 abuts against the second surface 163 of the partition member 160. Due to the diameter $D_W$ of the outer perimeter 137 of the end surface 136 of the second end 134 of the wick member 132 being greater than the diameter $D_{O2}$ of the second opening 172 and due to the relative positioning of the wick member 132 relative to the second opening 172, the outer perimeter 137 of the end surface 136 of the second end 134 of the wick member 132 surrounds the second opening 172 in the exemplified embodiment.

In the exemplified embodiment, the diameter $D_{O1}$ of the first opening 171 in the first surface 162 of the partition member 160 is greater than the diameter $D_W$ of the outer perimeter 137 of the end surface 136 of the second end 134 of the wick member 132. However, the invention is not to be so limited and in certain other embodiments the diameter $D_{O1}$ of the first opening 171 in the first surface 162 of the partition member 160 can be equal to or less than the diameter $D_W$ of the outer perimeter 137 of the end surface 136 of the second end 134 of the wick member 132. Furthermore, in the exemplified embodiment the wick member 132 has a constant diameter $D_W$. However, the invention is not to be so limited and in certain embodiments the diameter $D_W$ of the wick member 132 may increase or decrease from the second end 134 of the wick member to the first end 133 of the wick member 132.

Figure 3:
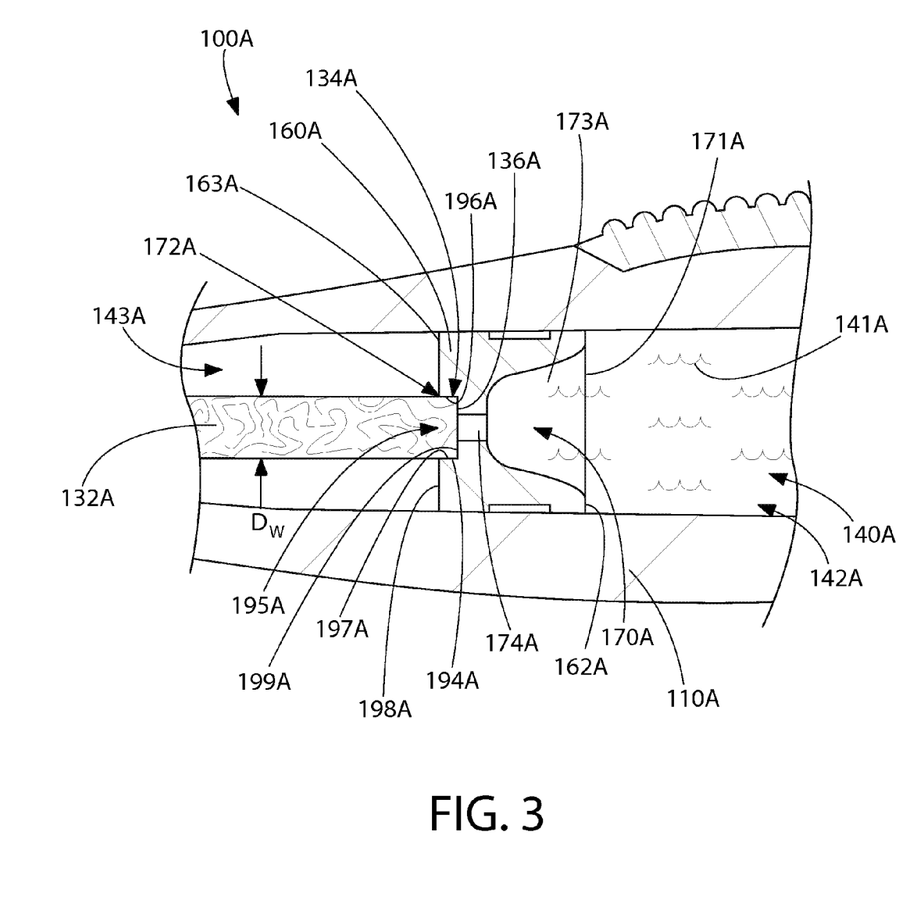
FIG. 3 is a first alternative embodiment of the close-up of FIG. 2.

Referring now to FIG. 3, an alternative embodiment of a portion of an oral care implement 100A will be discussed in accordance with the present invention. The embodiment exemplified in FIG. 3 is similar to the embodiment exemplified in FIG. 2 with the exception of the shape of the partition member 160A and the relative positioning between the partition member 160A and the wick member 132A. Thus, components of the oral care implement 100A that are similar to or the same as components of the oral care implement 100 described above will not be described herein below in the interest of brevity. Furthermore, components of the oral care implement 100A will be numbered similarly to the same components of the oral care implement 100 except that the suffix "A" will be used. Thus, it should be understood that those components of the oral care implement 100A that are numbered but not described herein below have a similar function and/or structure to the similar component illustrated in FIGS. 1 and 2 and described above.

The partition member 160A comprises a first surface 162A and a second surface 163A. Similar to the embodiment discussed above, the second surface 163A of the partition member 160A is a transverse surface. However, in FIG. 3 the transverse second surface 163A is a stepped surface. Specifically, the transverse second surface 163A comprises an upper surface 198A and a recessed surface 199A. Two opposing riser surfaces 196A, 197A extend from opposing ends of the recessed surface 199A to the upper surface 198A and form an annular shoulder. A socket 195A is formed between the opposing riser surfaces 196A, 197A having the recessed surface 199A as a floor of the socket 195A. In the exemplified embodiment, the width of the recessed surface 199A is substantially equal to the diameter $D_W$ of the wick member 132A. However, in certain other embodiments the width of the recessed surface 199A may be slightly larger than the diameter $D_W$ of the wick member 132A.

The partition member 160A comprises a first opening 171A in the first surface 162A of the partition member 160A and a second opening 172A in the second surface 163A of the partition member 160A. The wick member 132A comprises a second end 134A that terminates in an end surface 136A. In the exemplified embodiment, the end surface 136A of the second end 134A of the wick member 132A protrudes through the second opening 172A in the second surface 163A of the partition member 160A and abuts the recessed surface 199A of the second surface 163A of the partition member 160A. In the exemplified embodiment, the wick member 132A fits snugly within the socket 195A such that the outer surface 194A of the second end 134A of the wick member 132A is in contact with the riser surfaces 196A, 197A. However, in embodiments whereby the recessed surface 199A has a greater width than the width $D_W$ of the wick member 132A, the wick member 132A may not be in contact with both of the riser surfaces 196A, 197A.

The socket 195A further facilitates proper positioning of the wick member 132A to ensure that the end surface 136A of the second end 134A of the wick member 132A is in fluid communication with the delivery section 174A of the passageway 170A that extends through the partition member 160A. Furthermore, the end surface 136A of the second end 134A of the wick member 132A abuts the second surface 163A of the partition member 160A to prohibit axial movement of the wick member 132A in a first axial direction, the first axial direction being in a direction towards the storage chamber 142A of the internal reservoir 140A in the exemplified embodiment. Moreover, due to the positioning of the end surface 136A of the second end 134A of the wick member 132A relative to the delivery section 174A of the passageway 170A, all of the oral care fluid 141A flowing through the passageway 170A from the inlet section 173A to the delivery section 174A and towards the second opening 172A in the second surface 163A of the partition 160A will come into contact with the wick member 132A.

Figure 4:
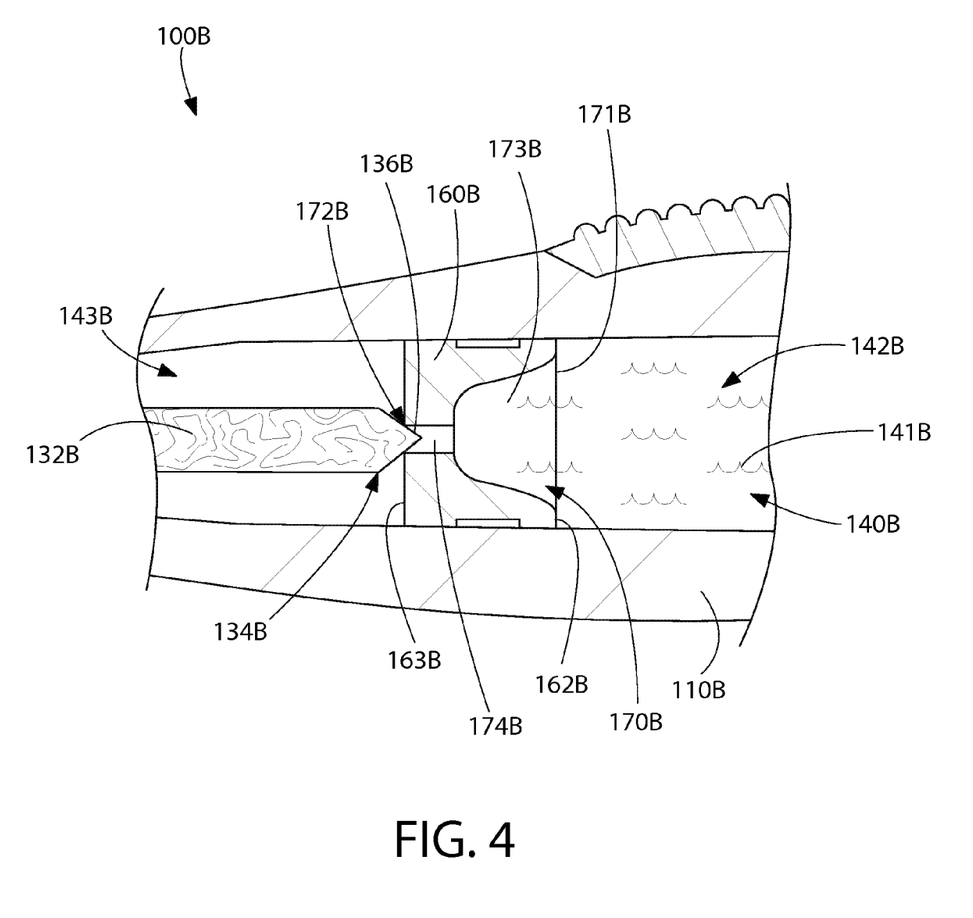
FIG. 4 is a second alternative embodiment of the close-up of FIG. 2.

Referring now to FIG. 4, another alternative embodiment of a portion of an oral care implement 100B will be discussed in accordance with the present invention. The embodiment exemplified in FIG. 4 is similar to the embodiment exemplified in FIG. 2 with the exception of the shape of the partition member 160B and the relative positioning between the partition member 160B and the wick member 132B. Thus, components of the oral care implement 100B that are similar to or the same as components of the oral care implement 100 described above will not be described herein below in the interest of brevity. Furthermore, components of the oral care implement 100B will be numbered similarly to the same components of the oral care implement 100 except that the suffix "B" will be used. Thus, it should be understood that those components of the oral care implement 100B that are numbered but not described herein below have a similar function and/or structure to the similar component illustrated in FIGS. 1 and 2 and described above.

In the embodiment exemplified in FIG. 4, the partition member 160B has a structure that is substantially similar to the partition member 160 illustrated in FIGS. 1 and 2. Specifically, the partition member 160B has a first surface 162B and a second surface 163B. A passageway 170B is formed through the partition member 160B. A first opening 171B is formed into the first surface 162B of the partition member 160B and a second opening 172B is formed into the second surface 163B of the partition member 160B.

The wick member 132B comprises a second end 134B that terminates in an end surface 136B that abuts the second surface 163B of the partition member 160B. In the exemplified embodiment, the end surface 136B of the second end 134B of the wick member 132B is conical. Thus, although a portion of the end surface 136B of the second end 134B of the wick member 132B is able to penetrate through the second opening 172B in the second surface 163B of the partition member 160B, a portion of the end surface 13B of the second end 134B of the wick member 132B still abuts against the second surface 163B of the partition member 160B. In this manner, the wick member 132B is prohibited from axial movement in a first axial direction towards the storage chamber 142B due to the end surface 136B of the second end 134B of the wick member 132B abutting against the second surface 163B of the partition member 160B.

The invention and inventive concepts described herein include various combinations of the embodiments illustrated in FIGS. 2, 3 and 4 as would be understood by persons of ordinary skill in the art. For example, the wick member 132B having the conical end surface 136B of FIG. 4 can be used with the partition member 160 illustrated in FIG. 2.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A toothbrush comprising:
    a handle extending along a longitudinal axis and having an internal reservoir containing an oral care fluid;
    a head coupled to the handle and having a plurality of tooth cleaning elements;
    an applicator located on the head;
    a partition member positioned within the internal reservoir that divides the internal reservoir into a storage chamber and an overflow chamber, the partition member comprising a first surface facing the storage chamber and a second surface facing the overflow chamber;
    a passageway extending through the partition member from the storage chamber to the overflow chamber, the passageway terminating as a first opening in the first surface of the partition member and as a second opening in the second surface of the partition member; and
    a wick member having a first end in fluid communication with the applicator and a second end terminating in an end surface in contact with the second surface of the partition member to prohibit axial movement of the wick member in a first axial direction.

2. The toothbrush according to claim 1 wherein the tooth cleaning elements extend from a front surface of the head and the applicator is located on a rear surface of the head.

3. The toothbrush according to claim 2 further comprising a channel extending from the overflow chamber to an opening on the rear surface of the head, a portion of the wick member located within the channel and the applicator exposed through the opening on the rear surface of the head.

4. The toothbrush according to claim 1 wherein the second surface of the partition member is a transverse surface.

5. The toothbrush according to claim 4 wherein the second surface of the partition member comprises an upper surface and a recessed surface; and wherein the end surface of the second end of the wick member abuts the recessed surface of the second surface of the partition member.

6. The toothbrush according to claim 1 wherein the end surface of the second end of the wick member is conical.

7. The toothbrush according to claim 1 wherein the end surface of the second end of the wick member has a diameter $D_W$ and wherein the second opening of the passageway has a diameter $D_{O2}$, the diameter $D_W$ of the end surface of the second end of the wick member being greater than the diameter $D_{O2}$ of the second opening.

8. The toothbrush according to claim 7 wherein the first opening of the passageway has a diameter $D_{O1}$, the diameter $D_{O1}$ of the first opening of the passageway being greater than the diameter $D_{O2}$ of the second opening of the passageway.

9. The toothbrush according to claim 1 wherein the end surface of the second end of the wick member has an outer perimeter that surrounds the second opening.

10. The toothbrush according to claim 1 wherein the partition member is positioned within the internal reservoir at a fixed axial location.

11. The toothbrush according to claim 1 wherein the first axial direction is towards the storage chamber.

12. The toothbrush according to claim 1 wherein the material that forms the partition member is selected from the group consisting of polypropylene, low density polyethylene, high density polyethylene, thermoplastic elastomer and thermoplastic vulcanizate.

13. The toothbrush according to claim 1 wherein the oral care fluid in the internal reservoir is delivered to the applicator solely by capillary action through the wick member.

14. The toothbrush according to claim 1 wherein the wick member comprises a first portion having a first capillarity and a second portion having a second capillarity, the first and second capillarities being different.

15. The toothbrush according to claim 1 wherein the wick member is integrally formed with the applicator.

16. A toothbrush comprising:
a handle extending along a longitudinal axis and having an internal reservoir containing an oral care fluid;
a head coupled to the handle and having a plurality of tooth cleaning elements;
an applicator located on the head;
a partition member positioned within the internal reservoir, the partition member separating the internal reservoir into a storage chamber and an overflow chamber, a passageway formed through the partition member and comprising an inlet section and a delivery section, the inlet section extending from the storage chamber to the delivery section, the delivery section extending from the inlet section to the overflow chamber, and wherein the inlet section has a maximum transverse cross-sectional area that is greater than a maximum transverse cross-sectional area of the delivery section; and
a wick member having a first end in fluid communication with the applicator and a second end that terminates in an end surface in fluid communication with the delivery section;
wherein the inlet section of the passageway terminates in a first opening in a first surface of the partition member that faces the storage chamber, and wherein the delivery section of the passageway terminates in a second opening in a second surface of the partition member that faces the overflow chamber;
wherein the end surface of the second end of the wick member contacts the second surface of the partition member to prohibit axial movement of the wick member in a first axial direction.

17. The toothbrush according to claim 16 wherein the partition member further comprises an upper section and an annular sidewall extending from the upper section in a direction towards the storage chamber, the annular sidewall comprising an inner surface that defines the inlet section and the upper section comprising an inner surface that defines the delivery section.

18. The toothbrush according to claim 17 wherein the inner surface of the annular sidewall is concave, the transverse cross-sectional area of the inlet section of the passageway decreasing with axial distance from the storage chamber.

19. The toothbrush according to claim 16 wherein the second surface of the partition member comprises an upper surface and a recessed surface, and wherein the end surface of the second end of the wick member is in contact with the recessed surface of the second surface of the partition member.

20. The toothbrush according to claim 16 wherein the end surface of the second end of the wick member having a perimeter portion that surrounds the second opening.

21. The toothbrush according to claim 16 wherein the partition member is positioned within the internal reservoir at a fixed axial location.

22. The toothbrush according to claim 16 wherein the end surface of the second end of the wick member has a transverse cross-sectional area that is greater than the maximum transverse cross-sectional area of the delivery section of the passageway.

23. A toothbrush comprising:
a handle extending along a longitudinal axis and having an internal reservoir containing an oral care fluid;
a head coupled to the handle and having a plurality of tooth cleaning elements;
an applicator located on the head;
a partition member positioned within the internal reservoir that divides the internal reservoir into a first chamber and a second chamber, the partition member comprising a first surface facing the first chamber and a second surface facing the second chamber;
a passageway extending through the partition member from the first chamber to the second chamber, the passageway terminating as a first opening in the first surface of the partition member and as a second opening in the second surface of the partition member; and
a wick member having a first end in fluid communication with the applicator and a second end terminating in an end surface having an outer perimeter that surrounds the second opening;
wherein the second opening in the second surface of the partition member has a first cross-sectional area and wherein the end surface of the second end of the wick member has a second cross-sectional area, the second cross-sectional area being greater than the first cross-sectional area.

24. The toothbrush according to claim 23 wherein axial movement of the wick member in a first axial direction towards the first chamber is prohibited.

25. The toothbrush according to claim 23 wherein the partition member is positioned within the internal reservoir at a fixed axial location.

26. The toothbrush according to claim 23 wherein the oral care fluid in the internal reservoir is delivered to the applicator solely by capillary action through the wick member.

* * * * *